United States Patent [19]

Shibata et al.

[11] Patent Number: 5,154,929
[45] Date of Patent: Oct. 13, 1992

[54] PERCUTANEOUS ABSORPTION TYPE PREPARATION AND PROCESS FOR PREPARING THE SAME

[75] Inventors: Keisuke Shibata; Yuusuke Ito; Saburo Otsuka; Shoichi Tokuda; Takashi Kinoshita, all of Osaka, Japan

[73] Assignee: Nitto Denko Corporation, Osaka, Japan

[21] Appl. No.: 740,662

[22] Filed: Aug. 2, 1991

Related U.S. Application Data

[63] Continuation of Ser. No. 336,149, Apr. 11, 1989, abandoned.

[30] Foreign Application Priority Data

Apr. 11, 1988 [JP] Japan .................... 63-88551

[51] Int. Cl.⁵ .............. A61F 13/00; A61F 13/02; A61L 15/00
[52] U.S. Cl. .................... 424/448; 424/447; 424/449
[58] Field of Search ............ 424/449, 448, 447

[56] References Cited

U.S. PATENT DOCUMENTS 4,719,226  1/1988  Otsuka et al. ................ 514/447
4,784,856  11/1988  Fukuda et al ................. 424/449

FOREIGN PATENT DOCUMENTS 0156080  12/1984  European Pat. Off. .
2095108  3/1981  United Kingdom .

OTHER PUBLICATIONS

Patent Abstracts of Japan, vol. 12, No. 242 (C-510)[3089].
European Search Report EP 89 10 6337.

*Primary Examiner*—Thurman K. Page
*Assistant Examiner*—James M. Spear
*Attorney, Agent, or Firm*—Sughrue, Mion, Zinn, Macpeak & Seas

[57] ABSTRACT

A percutaneous absorption type preparation and a process for preparing the same are disclosed. The preparation comprises a substantially drug-impermeable backing having provided thereon an adhesive layer comprising a pressure-sensitive adhesive containing therein a percutaneous absorption type drug (solid at room temperature) in an amount greater than the saturated solubility in the adhesive, wherein the excess amount of the drug greater than the saturated solubility is present in the adhesive in a continuous recrystallized state and a substantially network state.

10 Claims, No Drawings

PERCUTANEOUS ABSORPTION TYPE PREPARATION AND PROCESS FOR PREPARING THE SAME

This is a continuation of application Ser. No. 07/336,149 filed Apr. 11, 1989 now abandoned.

FIELD OF THE INVENTION

The present invention relates to a percutaneous absorption type preparation and a process for preparing the same. More particularly, the present invention relates to a percutaneous absorption type preparation comprising an adhesive layer which comprises a pressure-sensitive adhesive and a percutaneous absorption type drug present in the adhesive layer in an amount greater than the saturated solubility in the adhesive, the drug being held in the adhesive layer in a homogeneous and stable state, and a process for preparing the preparation.

BACKGROUND OF THE INVENTION

It is already known to administer a percutaneous absorption type drug through the skin by, for example, adhering to the skin or mucosa a polymer containing a percutaneous absorption type drug, and many methods thereof have been proposed in various patents, literatures, etc. The typical method comprises forming on a suitable backing an adhesive layer comprising a polymer which comprises a rubber or acrylic resin based pressure-sensitive adhesive admixed with a percutaneous absorption type drug.

The actual concentrations of the percutaneous absorption type drugs present in the adhesives have been equal to or less than the saturated solubility thereof in the pressure-sensitive adhesives. The reason for this is that even if the drug in excess of the saturated solubility is simply incorporated in the adhesive, large-sized crystal particles thereof are formed and remain in the adhesive layer without being absorbed through the skin.

On the other hand, a method has been proposed to absorb a drug through the skin without loss by adding a percutaneous absorption type drug to a pressure-sensitive adhesive in an amount greater than the saturated solubility as disclosed in, for example, U.S. Pat. No. 4,719,226.

According to this method, the amount of drug in excess of the solubility is dispersed in the adhesive layer as recrystallized fine particles, thereby allowing the drug to be absorbed through the skin without loss for a predetermined period of time.

Besides, it is known that the adhesive strength of the pressure-sensitive adhesive to the skin decreases with the lapse of time in addition to external factors. Therefore, if a pressure-sensitive adhesive having a low viscosity is used, the desired adhesion effect to the skin can be obtained, but there is the disadvantage that part of the adhesive remains on the skin (hereinafter referred to as "adhesive remaining problem"). On the other hand, if a pressure-sensitive adhesive having a high viscosity is used, the adhesive does not remain on the skin, but in some cases, the desired adhesion effect to the skin is obtained only for a short period of time.

Under the above circumstance, if the drug in excess amount above the saturated solubility in a pressure-sensitive adhesive is dispersed in the adhesive in the form of recrystallized fine particles, in the event that the pressure-sensitive adhesive has a high visocisity, there are the same disadvantages as described above and the edge peeling of a preparation occurs; and in the event that the adhesive has a low viscosity, since the excess amount of the percutaneous absorption type drug is dispersed in the form of recrystallized fine particles, the drug does not exhibit the function as fillers and the adhesive remaining problem still occurs.

SUMMARY OF THE INVENTION

Accordingly, one object of the present invention is to provide a percutaneous absorption type preparation, wherein even if the viscosity of a pressure-sensitive adhesive is a low viscosity, by making a percutaneous absorption type drug in an amount greater than its solubility present in the adhesive in the specific form, the drug exhibits a function as fillers, thereby causing no adhesive remaining problem, at the initial stage, and with the lapse of time, the adhesive properties are maintained together with dissolution of the recrystallized drug and the preparation does not peel off.

Another object of the present invention is to provide a process for preparing the preparation.

The percutaneous absorption type preparation according to the present invention comprises a backing which is substantially impermeable to a percutaneous absorption type drug, and an adhesive layer provided on the surface of the backing, which comprises a pressure-sensitive adhesive and a percutaneous absorption type drug (which is solid at room temperature), wherein the drug is present in the adhesive in an amount greater than its saturated solubility in the adhesive and the drug is present in the adhesive in the form of a continuous recrystallized state and also a substantially network state.

The process for preparing a percutaneous absorption type preparation according to the present invention comprises providing an adhesive layer comprising a pressure-sensitive adhesive containing therein a percutaneous absorption type drug (which is solid at room temperature) in an amount greater than its saturated solubility in the adhesive, on a surface of a backing which is substantially impermeable to the drug, and if desired, simultaneously adhering temporarily a release covering material on the adhesive layer, and applying a stimulation to the adhesive before the excess amount of the drug larger than the saturated solubility in the adhesive is recrystallized, to induce and accelerate the recrystallization of the drug, thereby making the drug present in a continuous crystallized state and also a substantially network state.

DETAILED DESCRIPTION OF THE INVENTION

The percutaneous absorption type preparation according to the present invention is such that the excess portion of the drug larger than its saturated solubility is continuously recrystallized in a substantially radial state, the continuously recrystallized drug is, although having a directionality as a whole, overlapped in the adhesive layer and shows substantially a network state when observed from the surface, and as a result, the recrystallized drug exhibits a function as fillers to prevent the adhesive remaining on the skin.

The state of recrystallized particles of the drug present in the adhesive described above is hereinbefore and hereinafter expressed as "the excess amount of the drug greater than the saturated solubility is present in the adhesive in a continuous crystallized state and also a substantially network state" or the similar phrases.

Examples of the backing which can be used include plastic films, composite films or sheets made of synthetic resins such as polyolefin, polyurethane, polyacrylate, polyester, polyvinylchloride, polyvinylidene chloride, polyamide, ethylene-based copolymer and vinyl chloride-vinyl acetate copolymer, porous (micro porous) films or sheets made of rubber and/or synthetic resins, fibrous film or sheets such as nonwoven fabrics, fabrics and paper, metallic foils, and the above films or sheets with metal deposited on the surface thereof. The backing provides a self-supporting property to the percutaneous absorption type preparation and functions to prevent the drug from migrating from the adhesive layer formed on one surface of the backing.

The thickness of the backing film is not particularly limited, and can be determined by taking into account a handling property, a feeling to the skin, etc. The thickness thereof is, however, generally in the range of from 5 to 300 μm.

The pressure-sensitive adhesive is a polymer (homopolymer or copolymer) having a good pressure-sensitive adhesive property composed only or mainly (at least about 50 wt %) of a rubber and/or synthetic resin which can maintain a percutaneous absorption type drug in an amount greater than the saturated solubility thereof in a continuous recrystallized state and continuously supply the drug to the surface of the skin. The apparent viscosity at room temperature (e.g., 15°–25° C.) of the polymer is $5 \times 10^6$ poise or less, preferably from $5 \times 10^3$ to $1 \times 10^6$ poise.

If the apparent viscosity at room temperature is more than $5 \times 10^6$ poise, the polymer is so hard that the adhesion to the skin becomes insufficient, and in some cases, the excess drug greater than the saturated solubility does not instantaneously form a continuously recrystallized state in preparing the pharmaceutical preparation. On the other hand, if the apparent viscosity is less than $5 \times 10^3$ poise, an adhesive may remain on the skin surface after peeling off the pharmaceutical preparation from the skin.

Pressure-sensitive adhesives having apparent viscosity at room temperature of $5 \times 10^6$ poise or less are obtained from rubbers such as a styrene-isoprene-styrene block copolymer rubber, a styrene-butadiene rubber, a polybutene rubber, a polyisopropylene rubber, a butyl rubber a silicone rubber, a natural rubber, a synthetic isoprene rubber and the like, and/or from synthetic resins such as poly(meth)acrylate, polyvinyl ether, polyurethane, polyester, polyamide, and ethylene-based copolymers. If desired and necessary, the polymer may contain additives such as a tackifying resin, a liquid rubber, and a softening agent, for example, to control the apparent viscosity of the adhesive at room temperature.

The polymers for the adhesives which are preferably used in the practice of the present invention are acrylate copolymers containing at least 50% by weight of acrylic or methacrylic acid alkyl esters where the average number of carbon atoms in the alkyl group is at least 4. The drug is highly soluble in these copolymers, and the copolymers do not irritate the skin or mucosa and maintain the drug in a stable manner.

The above acrylate copolymers include copolymers comprising the acrylic or methacrylic acid ester and functional monomers and/or vinyl ester monomers copolymerizable with the ester. The proportion of the functional monomer can range from 0 to about 20% by weight, preferably from 0.5 to 10% by weight, and the proportion of the vinyl ester monomer can range from 0 to about 40% by weight, preferably from 5 to 30% by weight.

The above functional monomers can be used to change the coagulation properties of the resulting copolymer depending on the amount of the functional monomer employed and also can be used to change the hydrophilic properties of the resulting copolymer depending on the type thereof. The above vinyl ester monomers can be used to increase the solubility of the drug in the copolymer.

Examples of suitable acrylic or methacrylic alkyl esters and functional monomers and vinyl ester monomers are shown below.

Acrylic or methacrylic alkyl esters:

n-butyl acrylate or methacrylate, hexyl acrylate, 2-ethylbutyl acrylate, isooctyl acrylate, 2-ethylhexyl acrylate or methacrylate, nonylacrylate, decyl acrylate or methacrylate, dodecyl acrylate or methacrylate, tridodecyl acrylate or methacrylate, etc.

Functional monomers:

acrylic or methacrylic acid, itaconic acid, maleic acid, maleic anhydride, hydroxyethyl acrylate, hydroxypropyl acrylate, methoxyethyl acrylate or methacrylate, ethoxyethyl acrylate or methacrylate, butoxyethyl acrylate, acryl or methacrylamide, dimethylacrylamide, dimethylaminoethyl acrylate or methacrylate,tert-butylaminoethyl acrylate or methacrylate, acrylonitrile, vinyl pyrrolidone, vinyl imidazole, etc.

Vinyl ester monomers:

vinyl acetate, vinyl propionate, etc.

Any percutaneous absorption type drugs can be used in the present invention so long as the drugs can be absorbed through the skin into the body when applied onto the skin and are solid at room temperature. Typical examples of such drugs are shown below.

Corticosteroids, analgesic anti-inflammatory agents, hypnotic sedatives, tranquilizers, antihypertensives, antihypertensive diuretics, antibiotics, anesthetics, antimicrobial agents, antifungal agents, vitamins, antiepileptics, coronary vasodilators, antihistaminic agents, antitussive antidepression agents sexual hormone, etc. Representative examples of those drugs are disclosed in, for example, U.S. Pat. No. 4,719,226 (columns 5-6).

The amount of the percutaneous absorption type drug added to the pressure-sensitive adhesive is generally about 60% by weight or less based on the weight of the adhesive. It is preferred that the amount of the percutaneous absorption type drug present be controlled such that the amount of the drug is at least 1.2 times, preferably 1.5 to 10 times, the saturated solubility of the drug in the polymer.

If the amount of the drug is less than 1.2 times, the amount of the continuous recrystallized particles in the adhesive forming the adhesive layer is too small and the desired lasting drug-releasing effect is difficult to obtain.

The percutaneous absorption type drug is added to the pressure-sensitive adhesive having a low viscosity at room temperature in an amount greater than its solubility in the polymer and dissolved therein uniformly in the presence of good solvent, the resulting mixture is applied on a backing and a stimulation is applied thereto, so that an adhesive layer comprising a drug dissolved in the range of its saturated solubility in the adhesive and a redissolvable continuous recrystallized drug present in the adhesive in a continuous recrystallized form and also a network form with a directionality can be obtained. The adhesive layer has adhesive properties conformable to a skin and firmly bonded and fixed on a backing which is substantially impermeable to the drug.

By selecting a good solvent, the redissolvable continuous recrystallized drug in the adhesive layer is continuously crystallized and precipitated from its dissolution state in a period of from several minutes to several hours by applying stimulation.

Thus, by making the percutaneous absorption type drug in an amount greater than its saturated solubility present in a continuous recrystallized state and also a substantially network state by applying stimulation, the drug exhibits the function as fillers, and the apparent viscosity at room temperature of the adhesive layer increases to a range of $7 \times 10^4$ to $6 \times 10^6$ poise, which is at least 2 times, preferably 2.5 to 50 times, larger than that of the pressure-sensitive adhesive prior to inclusion of the drug, thereby exhibiting excellent adhesive properties to the skin.

The thickness of the adhesive layer is from 5 to 500 μm, preferably from 10 to 300 μm. If the thickness is less than 5 μm, the adhesion to the skin is poor. On the other hand, if the thickness is more than 500 μm, the recrystallized particles are not uniform and no network state is formed due to localized recrystallization. As a result, the drug is not released uniformly.

Good solvents for the adhesives and the drugs which can be used to prepare the percutaneous absorption type preparation of the present invention include organic solvents such as ethyl acetate, chloroform, carbontetrachloride, methylene chloride, toluene, xylene, tetrahydrofuran, dioxane or acetone, mixtures of the above organic solvents and alcohols such as methyl alcohol and ethyl alcohol, and mixtures of the above mixtures and a small amount of water.

The adhesive and drug are uniformly dissolved in such a good solvent so that the amount of the drug is at least about 1.2 times the saturated solubility thereof in the adhesive to thereby prepare a solution having a solids content of from 10 to 40% by weight, preferably from 15 to 30% by weight, for preparation of an adhesive layer. This solution is coated on a backing in a dry thickness of from 5 to 500 μm, preferably from 10 to 300 μm, and dried at 20° to 180° C. for 0.5 to 30 minutes. If necessary and required, a releasing film (a film coated with a releasing agent) is temporarily adhered to the adhesive layer. A physical stimulation is applied to the adhesive layer containing the drug in an amount greater than its saturated solubility in the adhesive to induce and accelerate recrystallization of the drug, and as a result, a percutaneous absorption type preparation wherein the recrystallized drug is dispersed in a continuous recrystallized state and a substantially network state can be obtained.

A method of applying a physical stimulation to the adhesive layer is, for example, a method of giving a shearing and impactive stimulation to the adhesive layer. For instance, a perforation treatment by a needle-like material or a cylindrical material is applied to give a stimulation to the adhesive.

The excess drug in the adhesive to which a stimulation has been applied by the perforation treatment is such that the recrystallization thereof is induced and accelerated from the perforation portion to proceed in a continuous crystallized state and a substantially network state with a directionality, and connects the crystallized state which is proceeded from the neighboring perforation portion, and the whole recrystallization is completed.

Another stimulation applying method is a method wherein in obtaining a percutaneous absorption type preparation containing the drug in an amount designed from the preparation base sheet (e.g., a preparation sheet before cutting) comprising a backing and a percutaneous absorption type drug-containing adhesive layer, a stimulation is applied simultaneously when the base sheet is cut with a punching blade or a rotary blade. In this case, the crystals of the drug in a continuous recrystallized state and a substantially network state proceed inwardly from the edges of the preparation.

If desired, the adhesive layer may contain fillers such as fine silica powder, titanium white and calcium carbonate; absorption accelerating agents such as polyhydric alcohols, sulfoxides, amides, adipates, sebacates, laurates, salicylic acid, urea and allantoin; vehicles such as milk sugar, cyclodextrin and cellulose powder (which are generally mixed with the drug in advance); and compounding agents such as softening agents and anti-itch agents within the range of about 30% by weight or less for the purpose of increasing the volume, accelerating absorption or shape formability.

The percutaneous absorption type preparation of the present invention is designed in such a manner that an amount of the percutaneous absorption type drug in excess of the saturated solubility thereof in the pressure-sensitive adhesive is present in the pressure-sensitive adhesive in a continuous recrystallized state and a substantially network state. As a result, the percutaneous absorption type preparation of the present invention has the characteristic feature that the drug sufficiently exhibits a filler-like function to the pressure-sensitive adhesive having a low viscosity dissolution of the crystals with the lapse of time, resulting in decrease of the filler-like function thereof, ensures a good adhesion to the skin without presenting the problem of adhesive remaining.

Another characteristic feature is that since the continuous recrystallized particles of the drug are absorbed to the skin by sequential redissolving of the crystals starting from the region of the adhesive layer close to the skin, the preparation of the present invention has an excellent releasability over a long period of time.

In the process for producing the preparation, the system is uniformly dissolved using a good solvent, the resulting solution is applied on the backing, followed by drying, and a stimulation is applied thereto to form a continuous recrystallized state. Therefore, the recrystallization proceeds uniformly and there is no irregularity of recrystallization. As a result, a preparation having a stable releasability can be obtained.

Further, in applying a stimulation, use of cutting blade or perforation treatment can apply the stimulation to each portion simultaneously. Therefore, there is no irregularity of recrystallization in the preparation.

The present invention is described in greater detail by reference to the following non-limiting examples. All parts are by weight unless otherwise indicated.

EXAMPLE 1

The blend having the following components was polymerized in conventional manner to obtain a pressure-sensitive adhesive solution having an apparent viscosity at room temperature of $5 \times 10^4$ poise.

| 2-Ethylhexyl acrylate | 97 parts |
|---|---|
| Acrylic acid | 3 parts |
| Azobisisobutyronitrile | 0.2 parts |
| Ethyl acetate | 42.9 parts |

To 100 parts (calculated on a solid basis) of the solution was added 100 parts of ethyl acetate which was a good solvent for the above-prepared adhesive and a drug, in which 25 parts of isosorbide dinitrate (the saturated solubility thereof in the above pressure-sensitive adhesive: about 8% by weight) had been uniformly dissolved, and the mixture was then stirred to prepare a solution for an adhesive layer.

This solution was coated on a 12 μm thick polyester film in a dry thickness of 40 μm and dried at 100° C. for 4 minutes. A releasing film coated with a releasing agent was then temporarily provided on the above-prepared adhesive layer, and the percutaneous absorption type preparation was punched out therefrom using a cutting blade 5 cm square.

By the visual examination of the preparation obtained, it was found that the crystals of the drug were continuous in the shape of cedar leaves and dispersed in a substantially network state.

EXAMPLE 2

The base sheet of the preparation obtained in Example 1 was subjected to a perforation treatment using a blade planted with needles lengthwise and breadthwise at the interval of 5 mm, and, thereafter, the preparation of a predetermined size was obtained.

It was found that the crystallization of the drug was started from the perforation area and joined roughly at midpoints between perforations.

The concentrations in blood of Examples 1 and 2 are shown in Table 1 below.

TABLE 1

| Example No. | Concentration in Blood (ng/ml) | | | |
|---|---|---|---|---|
| | 12 hrs | 24 hrs | 36 hrs | 48 hrs |
| 1 | 310 | 290 | 250 | 200 |
| 2 | 260 | 270 | 240 | 220 |

COMPARATIVE EXAMPLE 1

The solution obtained in Example 1 was coated on a 12 μm thick polyester film in a dry thickness of 40 μm and dried at 90° C. for 5 minutes. A releasing film was provided thereon temporarily and the laminate was aged at room temperature for 48 hours to prepare a percutaneous absorption type preparation containing recrystallized fine particles having a mean particle diameter of about 5 μm.

COMPARATIVE EXAMPLE 2

The blend having the following components was polymerized in conventional manner to obtain a pressure-sensitive adhesive solution having an apparent viscosity at room temperature of $7 \times 10^5$ poise.

| 2-Ethylhexyl acrylate | 94 parts |
|---|---|
| Acrylic acid | 6 parts |
| Azobisisobutyronitrile | 0.2 parts |
| Ethyl acetate | 42.9 parts |

This solution was treated in the same manner as in comparative Example 1 to obtain a percutaneous absorption type preparation containing recrystallized fine particles having a mean particle diameter of about 5 μm.

The evaluation results of Examples 1 and 2 and Comparative Examples 1 and 2 with regard to adhesion to the skin and adhesive remaining with the lapse of time are shown in Table 2 below.

TABLE 2

| | Adhesion to skin with the lapse of time | | | | Adhesive remaining |
|---|---|---|---|---|---|
| | 12 hrs | 24 hrs | 36 hrs | 48 hrs | after removal |
| Example 1 | good | good | good | good | none |
| Example 2 | good | good | good | good | none |
| Comparative Example 1 | good | good | good | good | periphery |
| Comparative Example 2 | good | part | part | periphery | none |

Measurement Methods

Apparent Viscosity at room temperature:

This viscosity was measured using a creep-shear viscometer. A sample (10 mm in width and 20 mm in length) was adhered to a Bakelite panel, and the distance of movement of the sample in a very short time under a given load was read. The following equation gives the viscosity:

$$n = \frac{W \cdot l}{A} \times \frac{dt}{dx} \times 980$$

wherein
W: Load (g)
l: Thickness of the sample (cm)
A: Contact area (cm$^2$)
dx: Distance of movement in dt second (cm)

Adhesion to the skin with the lapse of time:

Sample sheets (5 cm×5 cm) were adhered to the breast of a male adult, and the adhesion was observed after 12, 24, 36 and 48 hours, respectively, based on the rating indicated below. After 48 hours, the sheet was peeled off and the state of adhesive remaining was evaluated on the basis of the rating indicated below.

Adhesion with the lapse of time:
  Good: No peeling
  Part: Partial peeling on the periphery
  Periphery: Almost all area on the periphery was peeled off
  Half: Half the area of sheet was peeled off Remaining adhesive:
  None: Adhesive remaining was not observed
  Part: Adhesive remained partially on the periphery
  Periphery: Adhesive remained on the whole periphery
  Remarkable: Adhesive remained on the whole area Concentration in blood:

Sample sheets (6 cm in diameter) were adhered to the back of a rabbit where the hair had been removed. After 12, 24, 36 and 48 hours, the blood was taken and the concentration of the drug in the blood was measured using gas chromatography.

EXAMPLES 3 TO 4 AND COMPARATIVE EXAMPLES 3 TO 6

The compositions as shown in Table 3 were used to prepare the preparations in the same manner as in Example 1.

TABLE 3

| | Example 3 | Comparative Example 3 | Comparative Example 4 | Example 4 | Comparative Example 5 | Comparative Example 6 |
|---|---|---|---|---|---|---|
| Composition | 75 Parts of nonylacrylate; 15 Parts of ethoxyethylacrylate; 10 Parts of vinyl acetate | 75 Parts of nonylacrylate; 15 Parts of ethoxyethylacrylate; 10 Parts of vinyl acetate | 60 Parts of nonylacrylate; 20 Parts of ethoxyethylacrylate; 20 Parts of vinyl acetate | 85 Parts of 2-ethylhexylacrylate; 15 Parts of N-vinyl-2-pyrrolidone | 85 Parts of 2-ethylhexylacrylate; 15 Parts of N-vinyl-2-pyrrolidone | 75 Parts of 2-ethylhexylacrylate; 25 Parts of N-vinyl-2-pyrrolidone |
| Apparent Viscosity (poise) | $1 \times 10^4$ | $1 \times 10^4$ | $4 \times 10^6$ | $5 \times 10^4$ | $5 \times 10^4$ | $1 \times 10^7$ |
| Name of drug | Flunitrazepam | Flunitrazepam | Flunitrazepam | Pindolol | Pindolol | Pindolol |
| Saturated Solubility (%) | 3.5 | 3.5 | 4 | 7 | 7 | 6 |
| Amount of Drug(parts) | 10 | 10 | 10 | 15 | 15 | 15 |
| Adhesion to the skin | | | | | | |
| After 12 hrs | Good | Good | Good | Good | Good | Good |
| After 24 hrs | Good | Good | Good | Good | Good | Part |
| After 36 hrs | Good | Good | Part | Good | Good | Periphery |
| After 48 hrs | Good | Good | Half | Good | Good | Half |
| Adhesive Remaining | None | Remarkable | None | None | Periphery | None |
| Concentration in Blood (mg/ml) | | | | | | |
| After 12 hrs | 28 | 30 | 32 | 50 | 47 | 50 |
| After 24 hrs | 40 | 40 | 36 | 45 | 45 | 40 |
| After 36 hrs | 35 | 39 | 25 | 41 | 40 | 29 |
| After 48 hrs | 30 | 35 | 16 | 37 | 35 | 11 |
| Stimulation Applied | Rectangular punching blade | None (particle diameter: 3 μm) | None (particle diameter: 2 μm) | * | None (particle diameter: 4 μm) | None (particle diameter: 4 μm) |

* Needle-like projections arranged in a lattice form at each distance of 12.5 mm While the invention has been described in detail and with reference to specific embodiments thereof, it will be apparent to one skilled in the art that various changes and modifications can be made therein without departing from the spirit and scope thereof.

What is claimed is:

1. A percutaneous absorption preparation comprising a drug-impermeable backing and an adhesive layer provided thereon which comprises a pressure-sensitive polymer adhesive and a percutaneous absorption drug (solid at room temperature) present in the adhesive layer in an amount which is at least 1.2 times its saturated solubility in the adhesive, wherein the excess drug in the adhesive layer is in a continuous recrystallized and networked state formed by applying a physical simulation to the adhesive which induces and accelerates recrystallization of the drug such that the excess drug is recrystallized in a continuous and networked state.

2. The preparation as claimed in claim 1, wherein the pressure-sensitive adhesive prior to the incorporation of the percutaneous absorption drug (solid at room temperature) has an apparent viscosity at room temperature of $5 \times 10^6$ poise or less.

3. The preparation as claimed in claim 2, wherein the pressure-sensitive adhesive prior to the incorporation of the percutaneous absorption drug (solid at room temperature) has an apparent viscosity at room temperature of from $5 \times 10^3$ to $1 \times 10^6$ poise.

4. The preparation as claimed in claim 1, wherein the amount of the drug present in the adhesive layer is 1.5 to 10 times its saturated solubility in the adhesive.

5. The preparation as claimed in claim 1, wherein the layer comprising the pressure-sensitive adhesive and the percutaneous absorption drug (solid at room temperature) has an apparent viscosity at room temperature of from $7 \times 10^4$ to $6 \times 10^6$ poise, which is at least two times the apparent viscosity at room temperature of the pressure-sensitive adhesive containing no drug.

6. The preparation as claimed in claim 1, wherein the apparent viscosity at room temperature of the pressure-sensitive adhesive containing the drug is 2.5 to 50 times the apparent viscosity of the pressure-sensitive adhesive containing no drug.

7. A process for producing a percutaneous absorption preparation which comprises:
dissolving in a solvent a pressure-sensitive adhesive and a percutaneous absorption drug (solid at room temperature) in an amount which is at least 1.2 times its saturated solubility in the adhesive to prepare a coating solution;
coating the coating solution on a surface of a backing which is impermeable to the drug;

drying the coating solution to form an adhesive layer; and applying a physical stimulation to the adhesive which induces and accelerates recrystallization of the drug, whereby the excess drug is recrystallized in the adhesive layer in a continuous and networked state.

8. The process as claimed in claim 7, wherein a releasing film is temporarily adhered on the adhesive layer prior to application of the physical stimulation.

9. The process as claimed in claim 7, wherein the physical stimulation is applied by a cutting blade.

10. The process as claimed in claim 7, wherein the physical stimulation is applied by a perforation treatment.

* * * * *